US 6,581,592 B1

(12) United States Patent
Bathe et al.

(10) Patent No.: US 6,581,592 B1
(45) Date of Patent: Jun. 24, 2003

(54) PURGE SYSTEM FOR NITRIC OXIDE ADMINISTRATION APPARATUS

(75) Inventors: Duncan P. L. Bathe, Madison, WI (US); Frederick J. Montgomery, Sun Prairie, WI (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 09/598,584

(22) Filed: Jun. 21, 2000

Related U.S. Application Data

(62) Division of application No. 08/857,925, filed on May 16, 1997, now Pat. No. 6,125,846.

(51) Int. Cl.[7] .............................................. A61M 16/00
(52) U.S. Cl. ............................ 128/202.22; 128/203.12; 128/203.14; 128/203.25
(58) Field of Search ....................... 128/200.24, 203.12, 128/203.14, 203.25, 204.21, 204.23, 205.23

(56) References Cited

U.S. PATENT DOCUMENTS

| 4,345,612 A | * | 8/1982 | Koni et al. | ............ | 137/101.19 |
| 4,461,293 A | * | 7/1984 | Chen | ............ | 128/204.23 |
| 4,462,398 A | * | 7/1984 | Durkan et al. | ............ | 128/200.14 |
| 4,506,666 A | * | 3/1985 | Durkam | ............ | 128/204.23 |
| 4,519,387 A | * | 5/1985 | Durkan et al. | ............ | 128/204.23 |
| 4,570,631 A | | 2/1986 | Durkan | | |

(List continued on next page.)

FOREIGN PATENT DOCUMENTS

| EP | 589751 | | 3/1994 |
| FR | 0589751 A1 | * | 9/1993 |
| WO | 92/10228 | * | 6/1992 |
| WO | 94/27664 | * | 12/1994 |
| WO | 95/1031 | * | 4/1995 |
| WO | 95/10315 | | 4/1995 |
| WO | 95/28193 | | 10/1995 |

OTHER PUBLICATIONS

Richard Channick, MD,An Ambulatory Delivery System and Initial Clinical Tests, Jun. 1995, vol. 109, pp. 1545–1549.*
Ronald Pearl, MD PHD, Inhaled Nitric Oxide, Mar. 1993, Anesthesiology, vol. 78 pp 413–415.*
"Pulsed Delivery of Inhaled Nitric Oxide to Patients with Primary Pulmonary Hypertension", Richard N. Channick, MD et al. Chest, vol. 109, p. 1545–1549, Jun. 1996.
"Inhaled Nitric Oxide, The Past, the Present, and the Future", Anesthesiology 78:413–416, Mar. 1993.
"Inhaled Nitric Oxide in Persistent Pulmonary Hypertension of the Newboard", Jesse D. Roberts et al., The Lancet, vol. 340; p. 818–820, Oct. 3, 1992.

Primary Examiner—Aaron J. Lewis
(74) Attorney, Agent, or Firm—Andrus, Sceales, Starke & Sawall, LLP

(57) ABSTRACT

A nitric oxide delivery system is disclosed that delivers a pulsed volume of NO containing therapeutic gas to a patient upon each inhalation of the patient. The NO delivery system includes certain functions to provide protection against the inadvertent inclusion of $NO_2$ in the therapeutic gas administered to the patient. One of the functions is to provide a purge upon start up of the delivery system apparatus that clears the regulator and conduits of any $NO_2$ that may have formed during the prior idle period of the system. A detector determines the start-up and may automatically carry out the purge cycle or may cause a prompt that is visual or audible to remind the user to carry out the purge cycle manually. As a further function, when the NO apparatus is terminated with respect to a patient, the system can, again, sense the termination or cessation of the therapy and automatically shut off the supply of NO containing gas at the source or provide an audible or visual prompt to remind the user to shut off the supply of the NO containing gas manually.

20 Claims, 3 Drawing Sheets

U.S. PATENT DOCUMENTS

| | | | | |
|---|---|---|---|---|
| 4,611,590 A | * | 9/1986 | Ryschka et al. | 128/203.14 |
| 4,612,928 A | * | 9/1986 | Tiep et al. | 128/204.23 |
| 4,677,975 A | * | 7/1987 | Edgar et al. | 128/200.14 |
| 4,685,456 A | * | 8/1987 | Smart | 128/205.22 |
| 4,686,975 A | * | 8/1987 | Naimon et al. | 128/204.23 |
| 4,705,034 A | * | 11/1987 | Perkins | 128/204.21 |
| 4,706,664 A | * | 11/1987 | Snook et al. | 128/204.23 |
| 4,873,971 A | * | 10/1989 | Perkins | 128/201.23 |
| 4,932,402 A | * | 6/1990 | Snook et al. | 128/204.23 |
| 4,991,576 A | * | 2/1991 | Henkin et al. | 128/203.28 |
| 5,005,570 A | * | 4/1991 | Perkins | 128/204.23 |
| 5,038,771 A | * | 8/1991 | Dietz | 128/204.21 |
| 5,099,836 A | * | 3/1992 | Rowland et al. | 128/204.23 |
| 5,099,837 A | * | 3/1992 | Russel et al. | 128/204.26 |
| 5,134,886 A | | 8/1992 | Ball | |
| 5,165,398 A | * | 11/1992 | Bird | 128/204.25 |
| 5,241,955 A | * | 9/1993 | Dearman et al. | 128/204.18 |
| 5,370,112 A | * | 12/1994 | Perkins | 128/204.21 |
| 5,531,218 A | | 7/1996 | Krebs | 128/203.12 |
| 5,558,083 A | * | 9/1996 | Bathe et al. | 128/203.12 |
| 5,560,353 A | * | 10/1996 | Willemot et al. | 128/204.21 |
| 5,603,315 A | | 2/1997 | Sasso, Jr. | 128/204.18 |
| 5,678,537 A | * | 10/1997 | Bathe et al. | |
| 6,125,846 A | * | 10/2000 | Bathe et al. | 128/202.22 |

* cited by examiner

PURGE SYSTEM FOR NITRIC OXIDE ADMINISTRATION APPARATUS

The present application is a divisional application of U.S. patent application Ser. No. 08/857,925, filed May 16, 1997, and now U.S. Pat. No. 6,125,846, issued Oct. 3, 2000.

BACKGROUND

This invention relates to the administration of a therapeutic gas such as nitric oxide (NO) to patients for therapeutic effect. In particular, it relates to a system wherein a controlled, predetermined dose of NO is provided to the patient with each inhalation by the patient and to the use of various functions utilized by that system to control and/or eliminate nitrogen dioxide ($NO_2$) from the system for safety reasons.

The function of the administration of NO has been fairly widely published and typical articles appeared in The Lancet, Vol. 340, October 1992 at pages 818–820 entitled "Inhaled Nitric Oxide in Persistent Pulmonary Hypertension of the Newborn" and "Low-dose Inhalational Nitric Oxide in Persistent Pulmonary Hypertension of the Newborn" and in Anesthesiology, Vol. 78, pgs. 413–416 (1993), entitled "Inhaled NO-the past, the present and the future".

The actual administration of NO is generally carried out by its introduction into the patient as a gas and commercially available supplies are provided in cylinders under pressure and may be at pressures of about 2000 psi and consist of a predetermined mixture of NO in a carrier gas such as nitrogen. A pressure regulator is therefore used to reduce the pressure of the supply cylinder to working levels for introduction to a patient.

The concentration administered to a patient will vary according to the patient and the need for the therapy but will generally include concentrations at or lower than 150 ppm. There is, of course, a need for that concentration to be precisely metered to the patient since an excess of NO can be harmful to the patient.

One current known method and apparatus for the administration of NO to patients is described in U.S. Pat. No. 5,558,083 where a system is provided that can be added to any ventilator and which will meter in the desired concentration of NO into the gas supplied from that ventilator.

Various other delivery devices have also been used that respond to the patient attempting to inhale to deliver a pulsed dose of NO to the patient and such pulsing devices have also been shown to have therapeutic effect on the patient, for example, as described in Higenbottam PCT patent application WO95/10315 and the publication of Channick et al "Pulsed delivery of inhaled nitric oxide to patients with primary pulmonary hypertension", Chest/109/June 1996. In such pulsatile dosing devices, a pulse of NO is administered to the patient as the patient inhales spontaneously.

The inhalation pulsing type devices are typically shown and described in Durkan, U.S. Pat. No. 4,462,398. Another such apparatus is described in pending U.S. patent application entitled "Constant Volume NO Pulse Delivery Device", filed on May 16, 1997, U.S. patent application Ser. No. 08/857,924, which was abandoned in favor of U.S. patent application Ser. No. 09/084,710, filed May 26, 1998, now U.S. Pat. No. 6,164,276, issued Dec. 26, 2000.

One difficulty with such devices that provide a supplemental therapeutic gas to the patient concerns the formation of $NO_2$ from NO. $NO_2$ is a toxic compound and its presence is, therefore, undesirable in any appreciable concentration in the gas administered to the patient. Such toxic effects are present at concentrations of about 5 ppm and therefore even minute quantities of $NO_2$ cannot be tolerated.

In the pulse dose devices that administer NO as a supplemental therapeutic gas to the patient, there is likely to be no monitor to sense the presence of $NO_2$ and therefore it is important to take preventative measures in the system itself to assure that the formation of $NO_2$ does not occur, or when it does occur, to remove the $NO_2$ from the system before the NO containing therapy gas is delivered to the patient.

The formation of $NO_2$ results from the reaction of NO with $O_2$ and therefore there is ample opportunity in the administration of NO to a patient for $NO_2$ to be formed. One possibility is when the administration device is connected to the NO therapy gas source, air can be trapped in the cylinder valve and regulator fittings when the connection is made and because the NO in the cylinder is typically only a few hundred parts per million even small volumes of air can provide enough oxygen to cause significant proportions of the NO to react and form $NO_2$. Another possibility is that air can be trapped in passages of the regulator and regulator pressure gauge and which are not in the main flow passages. The main passages are cleared of air during use by the flow of NO therapy gas from the cylinder, however, when the device is turned off for any length of time the $O_2$ in the air can diffuse out of these passages and can react with NO in the regulator and, if the cylinder valve is left open, the $O_2$ can diffuse into the cylinder and react with the NO in the cylinder. The reaction of NO and $O_2$ to form $NO_2$ is a time related reaction, that is, the more time that the NO is in association with the $O_2$, the more $NO_2$ is formed, therefore it is important to provide prevention measures wherever there is any time period where the NO and $O_2$ can be in contact with each other and provide means for removing the $NO_2$ from the system.

Two of the rather critical periods where sufficient time can elapse and where NO and $O_2$ may intermix and where the formation of $NO_2$ may therefore occur are during start-up where NO may have been left in the system in contact with $O_2$ from the prior use of the delivery system and also after a new cylinder has been attached to the delivery device and introduced new quantities of $O_2$ (in air) into the delivery device. Another critical period is the termination of the administration of NO to a patient and the delivery system shut off. At that latter time, unless the cylinder valve controlling the supply of NO containing therapy gas is turned to the off position to isolate the NO supply from the NO delivery system, there is the possibility that any $O_2$ remaining in the conduits of the regulator during the shut down period may migrate back into the cylinder of NO containing therapeutic gas and contaminate that cylinder of gas.

SUMMARY OF THE INVENTION

In accordance with the present invention, there is provided a nitric oxide delivery system where a volume of NO is administered to the patient and where certain safety steps are carried out to eliminate $NO_2$ from the system to prevent the inadvertent administration of a toxic concentration of $NO_2$ to the patient.

Therefore, as an aspect of the present invention, at the start up of the system, as indicated, there may be $NO_2$ that formed in the various conduits during the time period when the delivery system was idle. At this point, therefore, the system may, upon the initiation of start-up, provide a visual or audible prompt to the user to carry out the purge manually or, in the alternative, there may be an automatic purge at the initiation of that start-up. In either case, the purge rids the system of any $NO_2$ that may have formed during the time period the system was not in use.

As a further aspect of the present invention, the delivery system detects when the delivery of NO to the patient has been discontinued by the user and the system then either senses the discontinuance of the NO administration and provides a visual and/or audible prompt to the user so that the user can manually shut off the cylinder valve or, alternatively, automatically shuts off the cylinder valve to prevent $O_2$ from migrating back into the cylinder thereby isolating the NO supply from the various conduits and regulator of the NO delivery system. Completion of this step can be confirmed by the system by checking that the flow or pressure in the system goes to zero when a purge is performed after the cylinder valve is turned off. If the valve has not been turned off the pressure or flow during a purge will remain at previous levels and the system can continue the prompt to the user that the cylinder valve needs to be shut off.

DETAILED DESCRIPTION OF THE INVENTION

Figure 1:
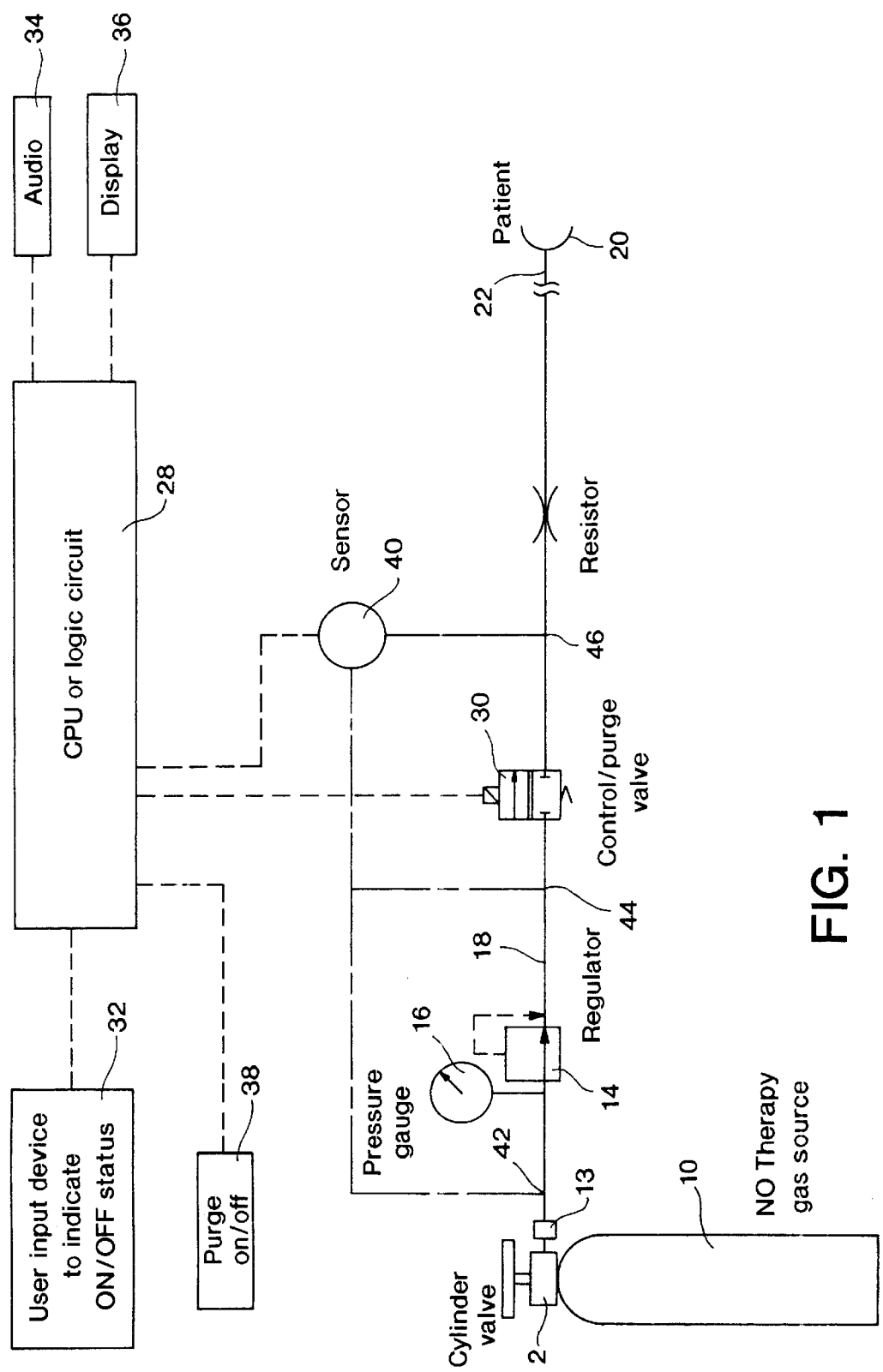
FIG. 1 is a schematic view of a NO delivery system constructed in accordance with the present invention where the user is prompted to perform the purge task.

Turning now to FIG. 1, there is shown a schematic view of a pulsed dosing nitric oxide (NO) delivery system constructed in accordance with the present invention. A gas cylinder 10 is provided containing the therapeutic amount of nitric oxide. Preferable that NO gas is mixed with a balance or carrier gas such as nitrogen and the concentration may be in the order of 100 ppm. The NO in nitrogen gas is available commercially in cylinders at pressures of approximately 2000 psig.

Atop the gas cylinder 10 is a cylinder valve 12 and which controls the supply of NO containing therapy gas to the overall NO delivery system. As will be explained, the cylinder valve 12 may be of the manually operated type or may be controlled by a remote signal, such as by an electrical signal operating a solenoid valve. A pressure regulator 14 is located just downstream of the cylinder valve 12 and reduces the cylinder pressure down to a working pressure for use with the present system and that pressure may be in the order of about 50 psig. The pressure regulator 14 is connected to the cylinder 10 by a connector 13. A pressure gauge 16 is generally provided on the pressure regulator 12 in order to keep track of the pressure within the gas cylinder 10.

A conduit 18 carries the NO containing therapy gas from the pressure regulator 14 through to a patient 20 where the NO containing therapy gas is administered to the patient by means such as a patient utilization device 22, an example of which is a nasal cannula (not shown). It is sufficient to note that the patient utilization device 22 has an opening that communicates the NO containing therapy gas to the patient for inhalation thereof.

A control valve 30 controls the flow of NO containing therapy gas from the gas cylinder 10 to the patient 20 and is a solenoid controlled valve operated by a signal from a controller 28 which may be a central processing unit (CPU), logic circuit or analog circuit. Again, for safety, the control valve 30 is preferably normally closed and is moved to its open position when a signal energizes the valve by the controller 28. The control valve 30 is operated by the controller 28 in accordance with timed or other means of sending pulses of NO containing therapy gas to the patient and the particular algorithm of control is not a part of the present invention.

A user input device 32 allows the user to turn the NO delivery system to the on or the off condition. The user input device 32, at the same time, signals the appropriate condition to the controller 28. Also as a part of the system, there may be an audio alarm 34 and/or a visual display 36 to alert the user to certain conditions of the NO delivery system.

A user purge input device 38 allows the user to initiate the purge cycle. The user purge input device 38, at the same time, signals the appropriate condition to the controller 28.

Sensor 40 is provided to act as a monitor of certain parameters in the NO delivery system and the sensor 40, as will become apparent, may be a flow sensor, a pressure sensor or the like and which may be connected to the conduit 18 to sense that parameter at a location 42 between the gas cylinder 10 and the pressure regulator 14, at a location 44 between the pressure regulator 14 and the control valve 30, or at a location 46 between the control valve 30 and the patient utilization device 22. As shown, the preferred location is at the location 46 and that sensor communication is shown as a solid line, the other locations 42 and 44 are indicated as dashed lines.

Figure 2:
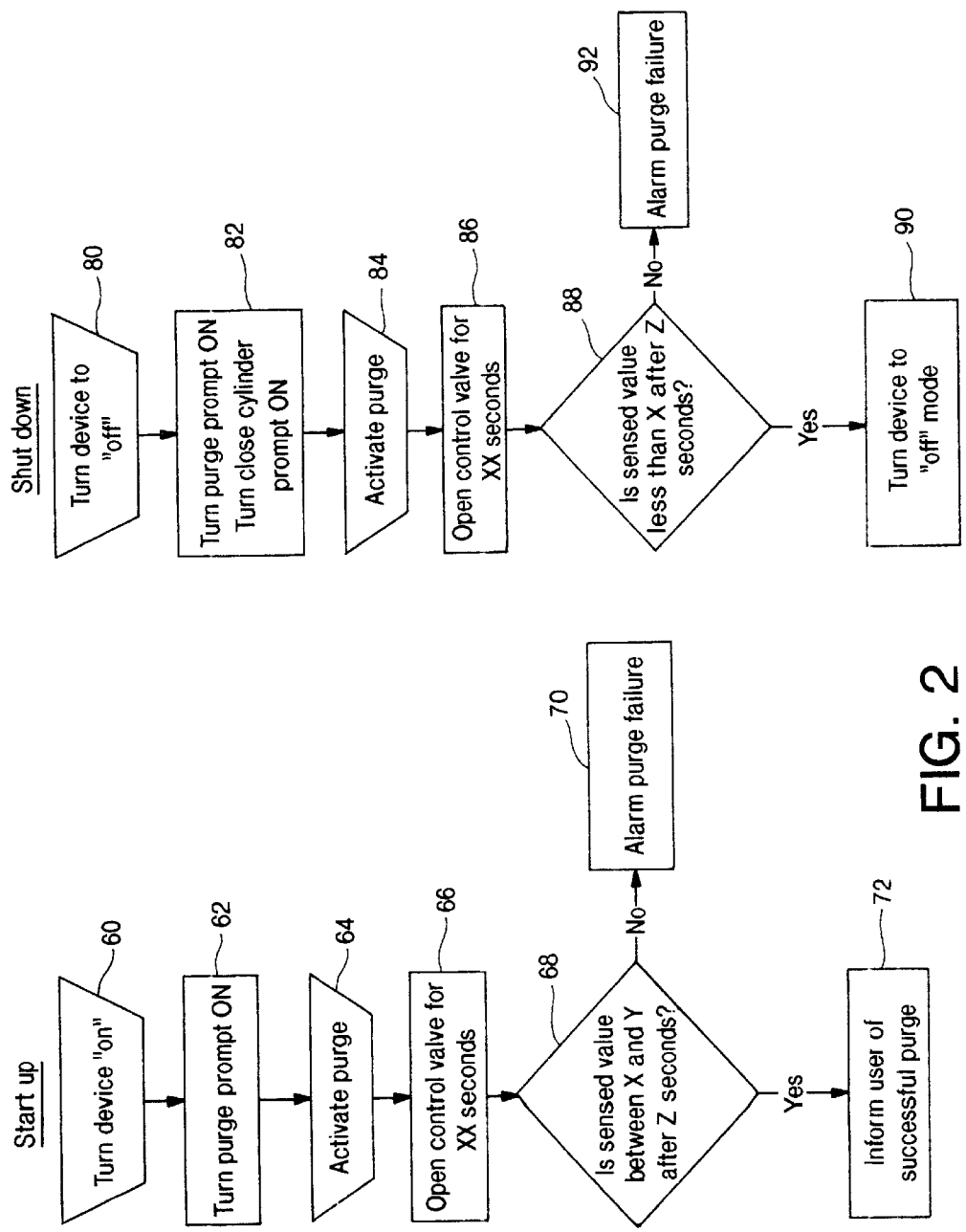
FIG. 2 is a logic diagram for a purge scheme using the NO delivery system shown in FIG. 1.

Turning now to FIG. 2, there is shown a flow chart, taken along with FIG. 1, and which describes the overall operation of the NO delivery system. As noted, upon start-up of the system, the gas cylinder 10 containing the NO therapy gas in a predetermined concentration is opened and the NO containing therapy gas enters the pressure regulator 14 and the conduit 18. The user initiates the NO delivery system by the user input device 32 being set to the on position, and which "on" signal is communicated to the controller 28.

At this point, since the NO delivery system is being initiated, there is a likelihood that some $NO_2$ may have formed in the conduit 18 or other parts of the delivery system since there may have been a considerable passage of time from the last use of the NO delivery system to allow the reacting of any remaining NO and $O_2$ to have occurred or a new therapy gas cylinder 10 could have been connected to the delivery system allowing air to enter the system at the connector 13. According, the system must be initially purged to assure that no $NO_2$ is present in any of the various components.

Upon the turning "on" of the device at 60, the controller 28 activates a purge prompt at 62 to inform the user to purge the system by audio alarm 34 and/or the visual display 36.

Activation of the purge at 64 by the user purge input device 38 opens the control valve 30 for a predetermined time at 66. During that time period the controller 28 determines if sufficient pressure, or flow, or the like, was present at 68 from the signal from sensor 40. As noted, the sensor 40 may be detecting various parameters of the gas in conduit 18, preferably flow or pressure.

If not, at 70 the controller 28 alerts the user that a purge was not successful by audible alarm 34 and/or the visual display 36.

If the sensor 40 detected sufficient pressure, or flow, or the like, at function 68 the controller 28 informs the user that a purge was performed successfully at 72 by the audible alarm 34 and/or the visual display 36.

Taking, now, the "shut down" cycle, upon the turning "off" of the device at 80, the controller 28 activates a purge prompt at 82 to inform the user to purge the NO delivery system by the audio alarm 34 and/or the visual display 36.

Activation of the purge at 84 by the user purge input device 38 opens the control valve 30 for a predetermined time at 86. During that time period the controller 28 determines if the pressure, or flow, or the like, from the signal from sensor 40, has decayed at 88 indicating that the cylinder valve 12 has been closed. The controller 28 then informs the user that a purge was performed successfully at 90 by the audible alarm 34 and/or the visual display 36.

If the sensor 40 detects that the pressure, or flow, or the like, has not decayed and therefore indicating that the cylinder valve 12 has not been closed, then the controller 28 alerts the user that a purge was not successful at 92, by the audible alarm 34 and / or the visual display 36.

Figure 3:
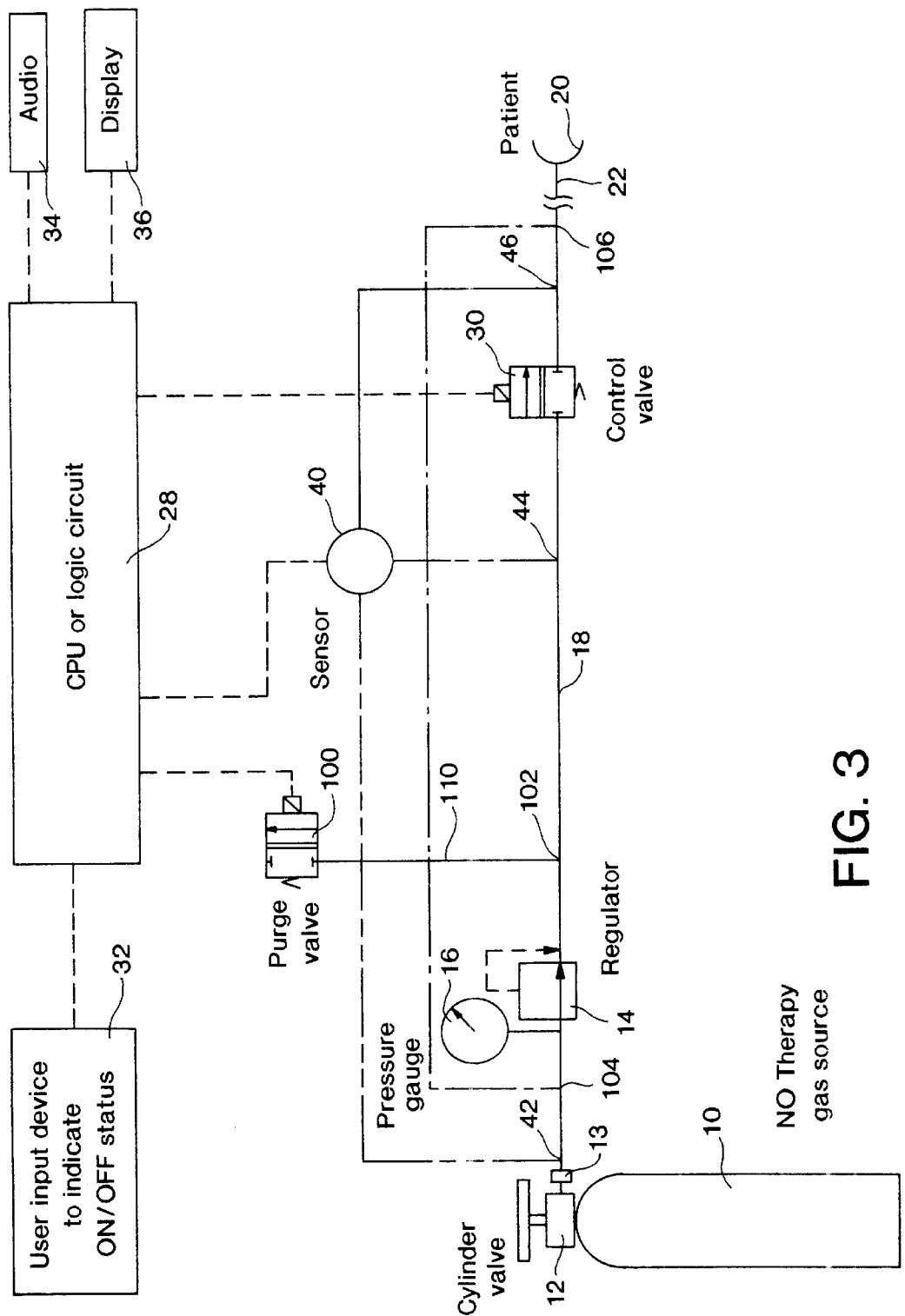
FIG. 3 is a schematic view of an alternative scheme where a purge valve is automatically actuated.

Turning now to FIG. 3, again taken in connection with FIG. 2, there is shown a schematic view of an alternate to the manual purge of FIG. 1. Teed off from the conduit 18 at location 102 is a purge line 110 and a purge valve 100. As can be seen, the purge valve 100 is normally in the non-energized position blocking the flow of gas therethrough and is activated by controller 28 to open the purge valve 100 to clear certain portions of the conduit 18 as well as pressure regulator 14 of gas. The location of the purge valve 100 could also be at locations 104 and 106. As shown, the preferred location is at the location 102 and that is shown as a solid line, the other locations 104 and 106 are indicated as dashed lines.

Again the logic as shown in FIG. 2 can apply except that the turning on of the purge prompt at 62 and the manual activation of the purge at 64 are made automatic by appropriate signals from the controller 28.

Similarly, during shut down, the logic steps at 82 and 84 are automated by the controller 28 by providing the appropriate signals.

In either event, upon the completion of the turn "on" purge cycle, the controller 28 will assume the control of the control valve 30 to carry out its normal function of opening and closing the control valve 30 to provide NO containing therapy gas to the patient 20.

Accordingly, by a mandatory purge carried out automatically or by prompt to the user, at the initiation of the use of the NO delivery system and a mandatory or user prompted bleed purge at the cessation of the NO delivery system along with a verification that the NO supply has been isolated from the delivery system, the $NO_2$ is effectively controlled and the possibility of $NO_2$ being inadvertently introduced to the patient during the NO therapy is greatly minimized, Numerous further variations and combinations of the features discussed above can be utilized without departing from the spirit of the invention as defined by the claims below. Accordingly, the foregoing description of the preferred embodiment should be taken by way of illustration rather than by way of limitation of the invention as claimed.

We claim:

1. A nitric oxide delivery system for delivering a series of therapeutic doses of nitric oxide (NO) in pulse form for administration to a patient while eliminating or lessening exposure of the patient to toxic nitrogen dioxide ($NO_2$) said system being connectable to a source of pressurized therapy gas containing NO, said system comprising;

a conduit adapted to be connected at one end to the pressurized therapy gas source, the other end of said conduit discharging therapeutic gas doses for administration to a patient;

a dosing valve in said conduit operable to repetitiously open and close to form the pulse doses of therapy gas containing NO;

a user input device operable by a user of the system to an activation condition upon start up of the system to render the nitric oxide delivery system operable;

control means responsive to the user input device being operated to the activation condition for automatically opening and thereafter closing said dosing valve to pass a quantity of therapy gas along said conduit to purge the conduit;

a sensor for sensing whether a physical parameter of the gas in said conduit has been altered as a result of an operation of said dosing valve when the system is started up to determine whether said valve has been automatically opened on start up to purge the conduit; and an indicator responsive to said sensor determining that purging of the conduit has been carried out for providing an indication to the user that the system may safely thereafter be used to administer therapeutic doses of nitric oxide to a patient.

2. A nitric oxide delivery system as defined in claim 1 wherein said sensor comprises a flow sensor.

3. A nitric oxide delivery system as defined in claim 1 wherein said sensor comprises a pressure sensor.

4. A nitric oxide delivery system as defined in claim 1 wherein said sensor senses a physical parameter of the gas in said conduit downstream of said dosing valve.

5. A nitric oxide delivery system as defined in claim 1 wherein said indicator is an audio alarm.

6. A nitric oxide delivery system as defined in claim 1 wherein said indicator is a visual display.

7. A nitric oxide delivery system for delivering a series of therapeutic doses of nitric oxide (NO) in pulse form for administration to a patient while eliminating or lessening exposure of the patient to toxic nitrogen dioxide ($NO_2$), said system being connectable to a source of pressurized therapy gas containing NO and having a source valve that can be opened and closed, said system comprising:

a conduit adapted to be connected at one end to the pressurized therapy gas source, the other end of said conduit discharging therapeutic gas doses for administration to a patient;

a dosing valve in said conduit operable to repetitiously open and close to form the pulse doses of therapy gas containing NO;

a user input device operable by a user of the system to an inactivation condition for shutting down the nitric oxide delivery system;

control means for automatically opening and thereafter closing said dosing valve when said user input device is operated to the inactivation condition;

a sensor for sensing whether or not a reduction in a physical parameter of the gas in said conduit occurs as a result of an opening of said dosing valve when the system is being shut down to determine whether the source valve of the pressurized therapy gas source has been closed; and an indicator responsive to said sensor sensing that a decay in a physical parameter of the gas has not occurred for providing an indication prompting the user to close the source valve of the pressurized therapy gas source when said delivery system is being shut down.

8. A nitric oxide delivery system as defined in claim 7 wherein said indicator is further defined as providing an indication prompting the user to close the source valve of the pressurized therapy gas source when the user input device is operated to the inactivation condition.

9. A nitric oxide delivery system as defined in claim 7 wherein said sensor comprises a flow sensor.

10. A nitric oxide delivery system as defined in claim 7 wherein said sensor comprises a pressure sensor.

11. A nitric oxide delivery system as defined in claim 7 wherein said sensor senses a physical parameter of the gas in said conduit downstream of said dosing valve.

12. A nitric oxide delivery system as defined in claim 7 wherein said indicator is an audio alarm.

13. A nitric oxide delivery stem as defined in claim 7 wherein said indicator is a visual display.

14. A nitric oxide delivery system for delivering a series of therapeutic doses of nitric oxide (NO) in pulse form for administration to a patient while eliminating or lessening exposure of the patient to toxic nitrogen dioxide ($NO_2$), said system being connectable to a source of pressurized therapy gas containing NO and having a source valve that can be opened and closed, said system comprising:

- a conduit adapted to be connected at one end to the pressurized therapy gas source, the other end of said conduit discharging therapeutic gas doses for administration to a patient;
- a dosing valve in said conduit operable to repetitiously open and close to form the pulse doses of therapy gas containing NO;
- a user input device operable by a user of the system to an activation condition upon start up of the system to render the nitric oxide delivery system operable and to an inactivation condition for shutting down the nitric oxide delivery system;
- control means for automatically opening said dosing valve when said user input device is operated to the activation condition and to the inactivation condition, the opening of the dosing valve when the user input device is operated to the activation condition passing a quantity of therapy gas along said conduit to purge the conduit when the source valve is open;
- a sensor for sensing whether a physical parameter of the gas in said conduit has been altered as a result of an operation of said dosing valve when the system is started up to determine whether said valve has been automatically opened on start up to purge the conduit, said sensor sensing whether or not a reduction in a physical parameter of the gas in said conduit has occurred as a result of an opening of said valve when the system is shut down to determine whether the source valve has been closed by the user; and
- an indicator responsive to said sensor and providing an indication to the user, said indicator being responsive to said sensor determining that purging of the conduit has been carried out for providing an indication to the user that the system may safety thereafter be used to administer therapeutic doses of nitric oxide to a patient, said indicator being responsive to said sensor sensing that a decay in a physical parameter of the gas has not occurred for providing an indication prompting the user to close the source valve of the pressurized therapy gas source when the delivery system is being shut down.

15. A nitric oxide delivery system as defined in claim 14 wherein said indicator is further defined as providing an indication prompting the user to close the source valve of the pressurized therapy gas source when the user input device is operated to the inactivation condition.

16. A nitric oxide delivery system as defined in claim 14 wherein said sensor comprises a flow sensor.

17. A nitric oxide delivery system as defined in claim 14 wherein said sensor comprises a pressure sensor.

18. A nitric oxide delivery system as defined in claim 14 wherein said sensor senses a physical parameter of the gas in said conduit downstream of said dosing valve.

19. A nitric oxide delivery system as defined in claim 14 wherein said indicator is an audio alarm.

20. A nitric oxide delivery system as defined in claim 14 wherein said indicator is a visual display.

\* \* \* \* \*